(12) United States Patent
Ross

(10) Patent No.: US 9,572,687 B2
(45) Date of Patent: Feb. 21, 2017

(54) NATIVE VERSION ALIGNMENT DEVICES AND METHODS

(71) Applicant: Matthew S. Ross, Redondo Beach, CA (US)

(72) Inventor: Matthew S. Ross, Redondo Beach, CA (US)

(73) Assignee: Matthew S. Ross, Harrisburg, PA (US)

( * ) Notice: Subject to any disclaimer, the term of this patent is extended or adjusted under 35 U.S.C. 154(b) by 376 days.

(21) Appl. No.: 14/228,204

(22) Filed: Mar. 27, 2014

(65) Prior Publication Data
US 2015/0073426 A1 Mar. 12, 2015

Related U.S. Application Data

(60) Provisional application No. 61/805,752, filed on Mar. 27, 2013, provisional application No. 61/811,615, filed on Apr. 12, 2013.

(51) Int. Cl.
| A61F 2/46 | (2006.01) |
|---|---|
| A61B 17/88 | (2006.01) |
| A61F 2/40 | (2006.01) |
| A61B 17/56 | (2006.01) |
| A61B 17/68 | (2006.01) |
| A61B 17/90 | (2006.01) |
| A61F 2/36 | (2006.01) |

(52) U.S. Cl.
CPC ............ *A61F 2/4657* (2013.01); *A61B 17/56* (2013.01); *A61B 17/88* (2013.01); *A61B 90/06* (2016.02); *A61F 2/40* (2013.01); *A61F 2/46* (2013.01); *A61B 2017/564* (2013.01); *A61B 2017/681* (2013.01); *A61B 2017/90* (2013.01); *A61B 2090/061* (2016.02); *A61B 2090/067* (2016.02); *A61F 2/36* (2013.01); *A61F 2002/4658* (2013.01); *A61F 2002/4668* (2013.01)

(58) Field of Classification Search
CPC ............. A61B 17/56; A61B 2017/564; A61B 2017/681; A61B 17/88; A61B 2017/90; A61B 90/06; A61B 2090/061; A61B 2090/067; A61F 2/36; A61F 2/40; A61F 2/46; A61F 2/4657; A61F 2002/4658; A61F 2002/4668
See application file for complete search history.

(56) References Cited

U.S. PATENT DOCUMENTS

| 2011/0275958 A1* | 11/2011 | Barrett | A61B 5/1071 600/595 |
|---|---|---|---|
| 2012/0296339 A1* | 11/2012 | Iannotti | A61B 17/15 606/87 |
| 2013/0006254 A1* | 1/2013 | Berberich | A61B 17/1764 606/88 |
| 2014/0276866 A1* | 9/2014 | Endsley | A61F 2/4657 606/89 |

* cited by examiner

*Primary Examiner* — Larry E Waggle, Jr.
(74) *Attorney, Agent, or Firm* — Baker & Hostetler LLP

(57) ABSTRACT

Devices and methods for aiding practitioners in the implementation of arthroplasty prosthetics. Example devices may include a base and an alignment arm, and may be used for finding and recording the native alignment of a bone head, such as the femoral or humeral head. The base may be attached to the bone and the alignment arm may be adjusted to reflect the native alignment of the bone. Once the alignment is recorded, the native bone head may be removed and the prosthetic bone head may be attached to the bone, and properly oriented using the alignment arm of the device.

5 Claims, 8 Drawing Sheets

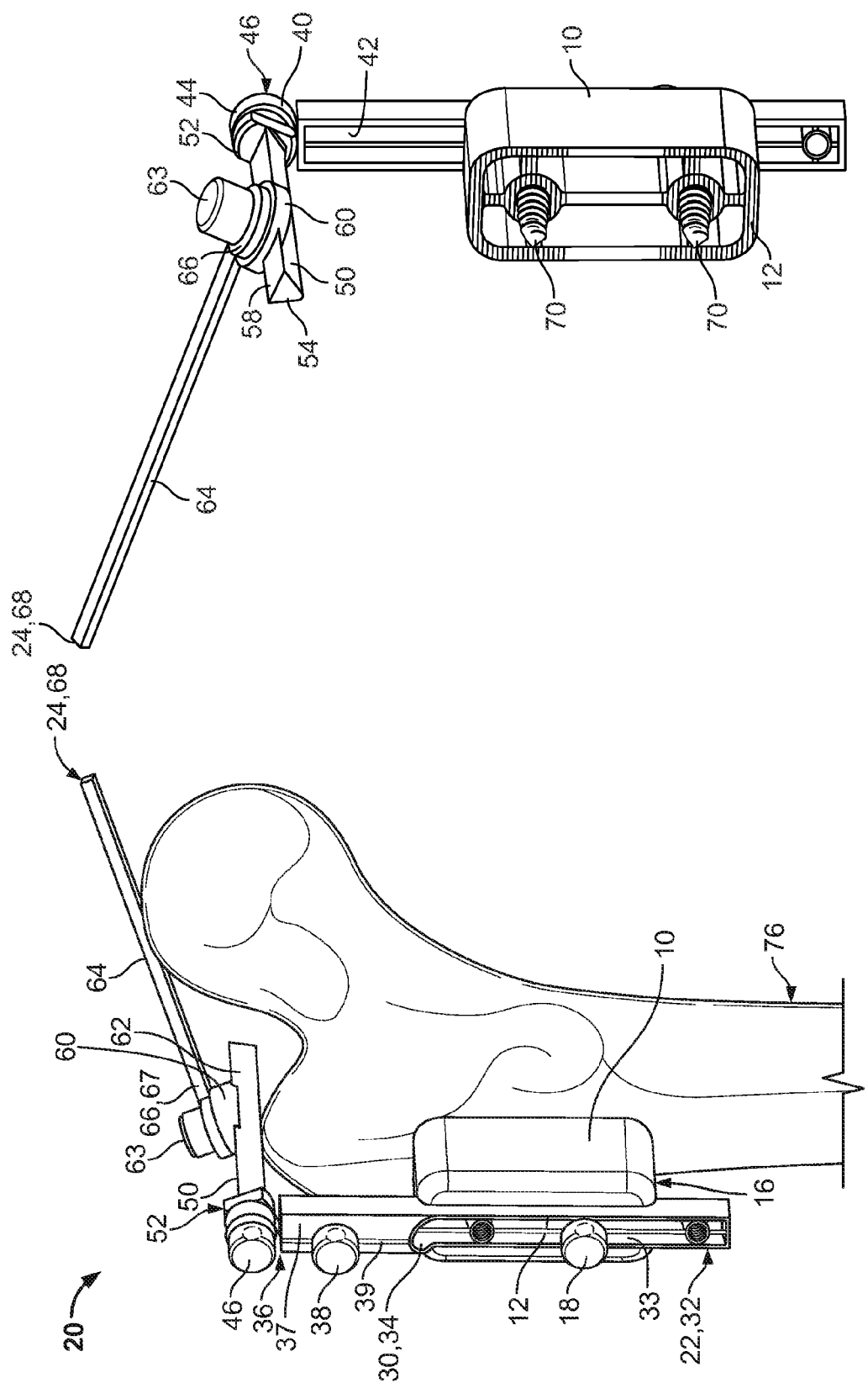

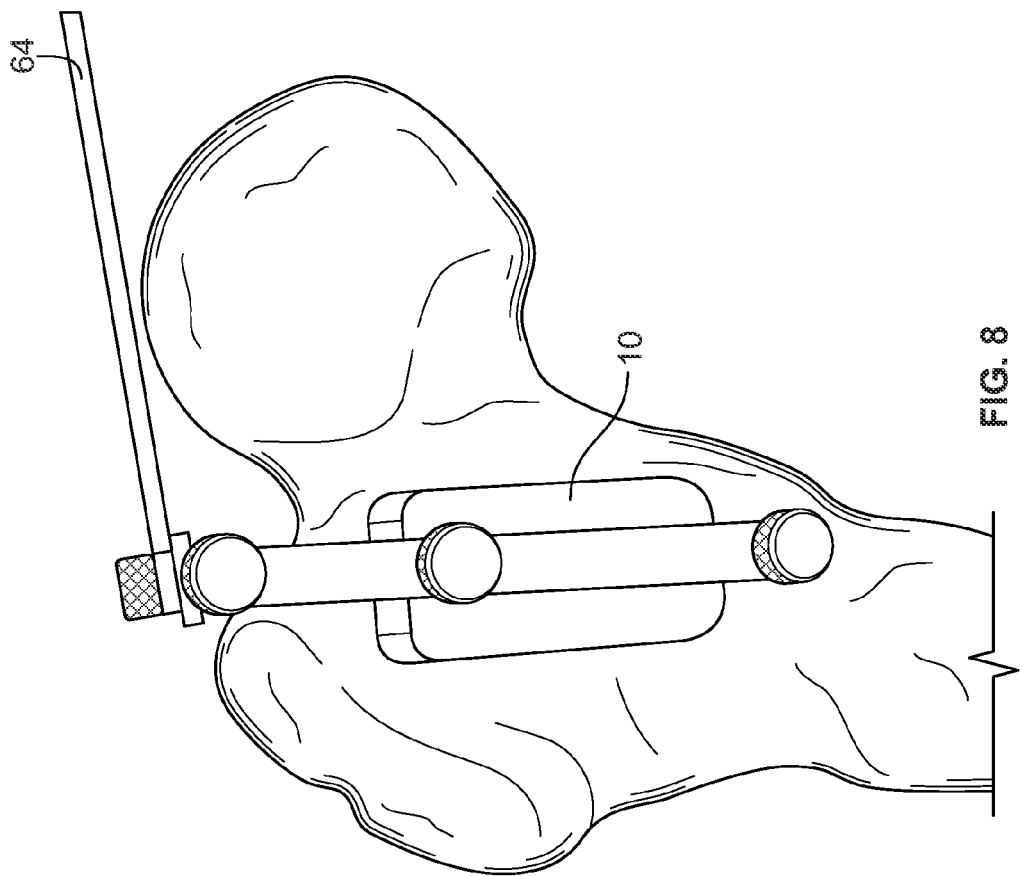
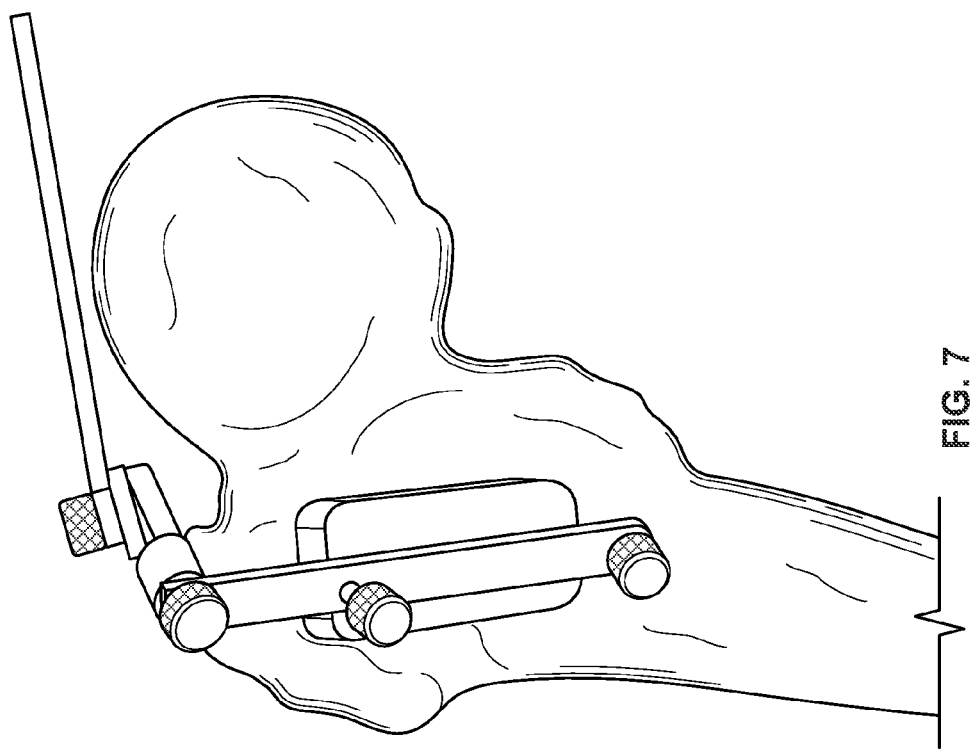

NATIVE VERSION ALIGNMENT DEVICES AND METHODS

CROSS REFERENCE TO RELATED APPLICATIONS

This application claims the benefit of U.S. Provisional Patent Application Ser. No. 61/805,752, titled "Native Version Alignment Device," filed on Mar. 27, 2013, the disclosure of which is incorporated herein by reference. This application also claims the benefit of U.S. Provisional Patent Application Ser. No. 61/811,615, titled "Native Version Alignment Device," filed Apr. 12, 2013, the disclosure of which is incorporated herein by reference.

BACKGROUND

Prosthetic bone implantation and joint replacement is well known in the art. Proper alignment of the implanted prosthesis is critical to the long term success of the implantation, and improper positioning can cause instability, impingement and increased wear. Misalignment of a prosthesis can also lead to soft tissue imbalance, joint dislocation, compromised range of motion and increased pain to the patient.

Having been in use since the mid-20$^{th}$ century, a conventional method of aligning a prosthesis relies on a statistical range of alignment values based on statistical anatomic studies. Using the statistical range as a guide, the surgeon visually estimates the proper angle to implant the prosthesis. As an example, for implantation of a humeral prosthesis, the statistical range for the retroversion angle is about 25 degrees to about 35 degrees based on anatomical studies. However, the retroversion angle can vary up to about 82 degrees and may be influenced by such factors as age, sex, race, and handedness. Similar variability exists for other prosthetic implants and alignment variables in other joints such as the femur for hip arthroplasty procedures.

Some researchers have experimented with computer-aided navigation systems. However, the utility of computer-aided navigation systems has not been fully explored, and the technique is expected to increase surgical times, particularly with medical professionals new to such technology. Preoperative CT scans can also be used to determine the proper alignment, but use of this technique results in increased radiation exposure to the patient, which is undesirable. Some mechanical devices to align prosthetic implants exist, but these devices rely on the statistical average range of alignment values based on the anatomical studies and do not account for the full range of variability. These devices do not re-create the native alignment and, therefore, often result in misalignment leading to the aforementioned consequences.

BRIEF SUMMARY

Examples of the present disclosure are directed to a device and methods for using such a device that may be applied intraoperatively to the proximal femur or humerus near the operative joint that is aligned to the native version of the patient's femoral or humeral head and neck allowing for implantation of the arthroplasty prosthesis in the same version as the native head and neck. Examples of the present disclosure may measure the height of the native femoral or humeral head and allow for implantation of the prosthesis with the same height as the native head. An example provides a prosthetic alignment device for an implantable prosthesis for an arm or leg joint that includes: a base configured to be coupled to the bone of the arm or leg approximate the joint, and an alignment arm coupled to the base, where the alignment arm includes: (a) a central core longitudinally adjustable with respect to the base along a longitudinal axis generally corresponding to the length of the bone; (b) a swivel arm horizontally extending from a distal end of the central core and rotatable about an axis generally perpendicular to the longitudinal axis of the central core; and (c) a version arm extending perpendicular from and laterally adjustable with respect to the swivel arm.

An example may be a surgical device for properly aligning a prosthesis to the native version alignment of a bone and comprising a base plate, an alignment arm and one or more fasteners for securing the base plate to the existing bone. The base plate has an outer surface and an underside surface such that the underside surface attaches to the bone and the outer surface faces away from the bone. The alignment arm has a proximal end and a distal end. The proximal end adjustably attaches to the outer surface of the base plate by a second fastener or fasteners. The alignment arm may be detached and removed from the base plate. The distal end of the alignment arm adjusts in 3-dimensions to assist in determining the proper alignment position for a prosthesis.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings.

In the drawings:

FIG. 1 is a perspective view of an example alignment device according to the current disclosure mounted to a bone.

FIG. 2 is another perspective view of the alignment device of FIG. 1.

FIG. 7 is a perspective view of the example alignment device of FIG. 6 mounted to a bone.

FIG. 8 is a side view of the example alignment device of FIGS. 6 and 7 mounted to a bone.

DETAILED DESCRIPTION

Figure 4:
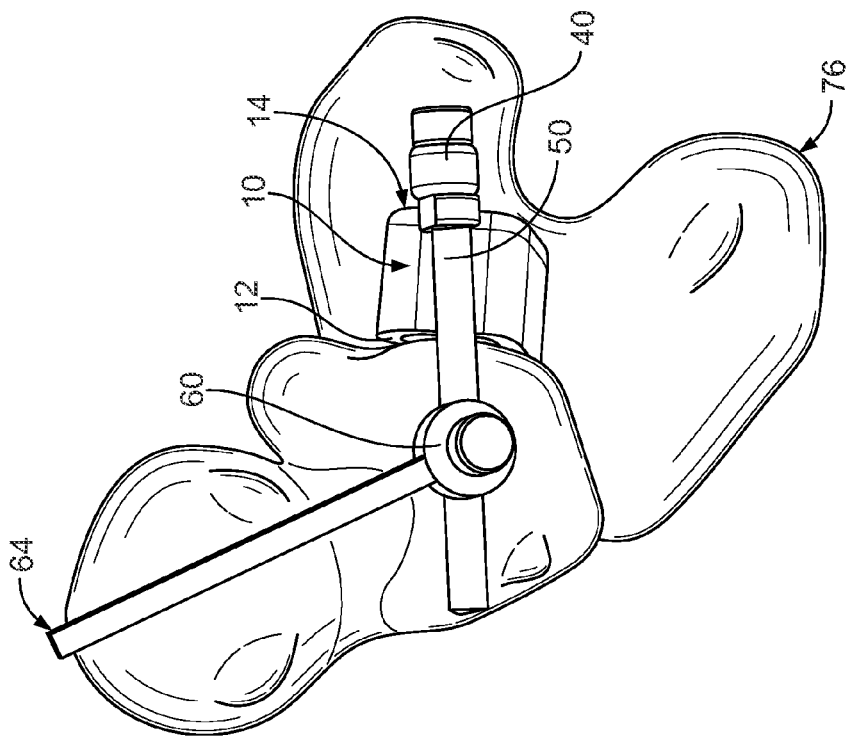
FIG. 4 is a top view of the example alignment device of FIGS. 1-3 attached to a bone.
Figure 3:
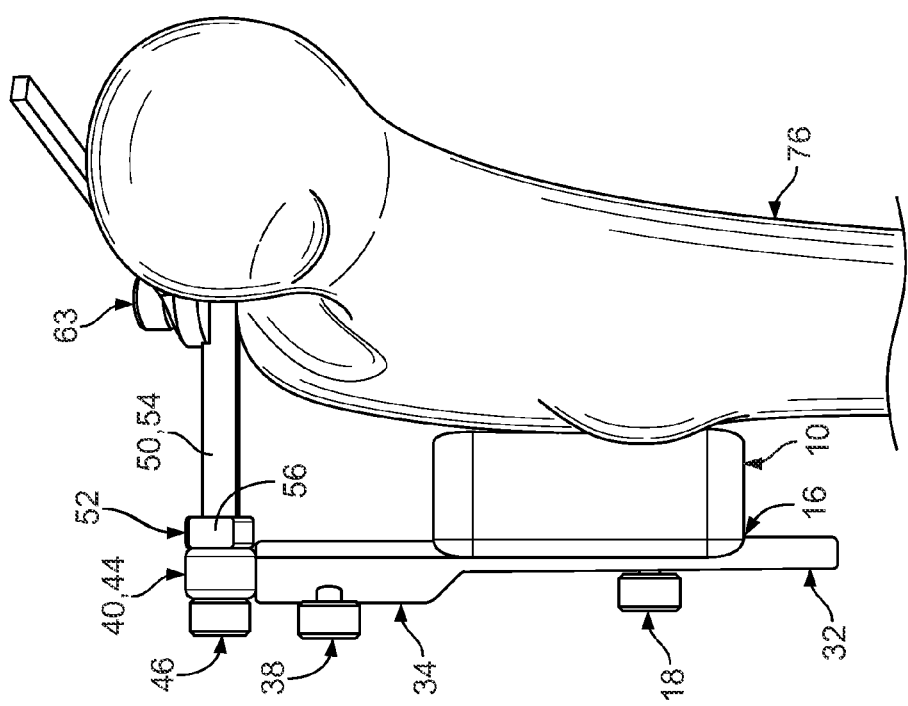
FIG. 3 is a side view of the example alignment device of FIGS. 1 and 2 attached to a bone.
Figure 6:
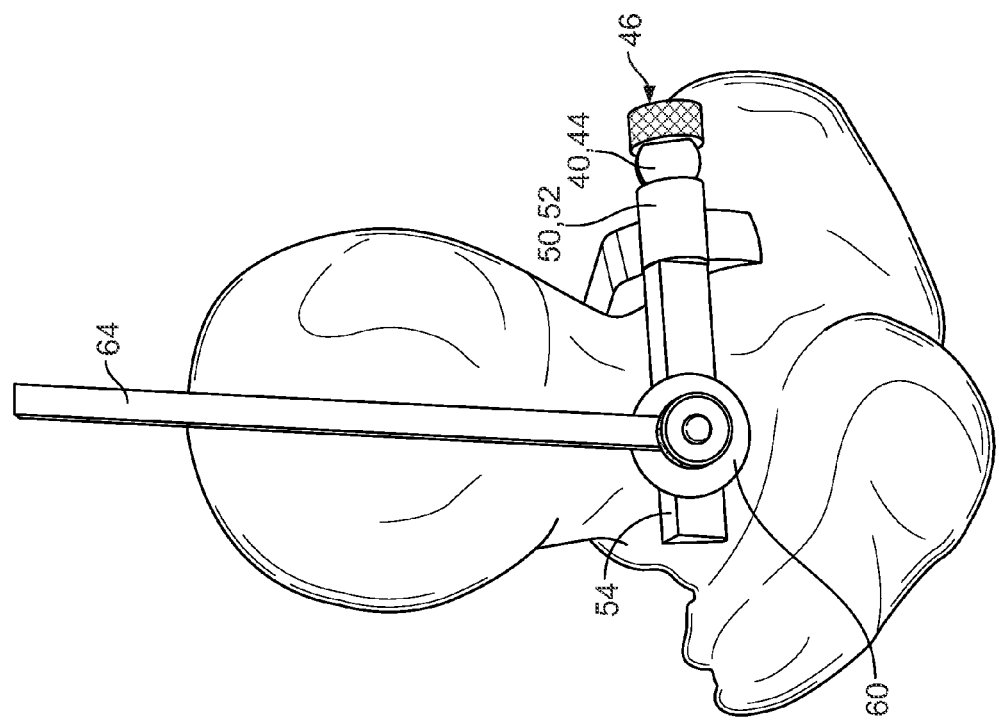
FIG. 6 is a top view of another example alignment device according to the current disclosure mounted to a bone.
Figure 5:
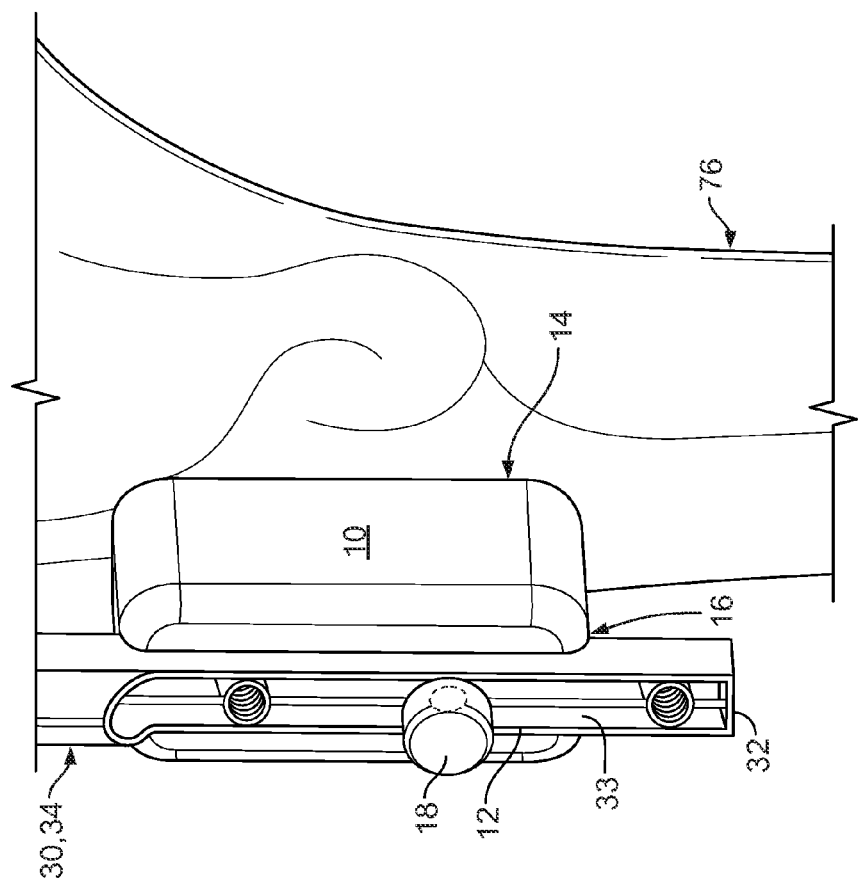
FIG. 5 is a close-up perspective view of an example base plate component of the alignment device of FIGS. 1-4 coupled to the bone.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of the present disclosure.

The present disclosure is generally directed to a surgical device for properly aligning a prosthesis to the native version alignment and methods of aligning a prosthesis. Some example surgical devices may include a base plate 10, an alignment arm 20 and one or more fasteners 70 for securing the base plate to the existing bone 76. The base plate 10 may attach to the bone 76 to which the prosthesis is to be aligned and implanted, and the proximal end 22 of the alignment arm 20 may attach to the base plate 10 by a fastener 70 or fasteners. The alignment arm 20 may be detached and removed from the base plate 10. The alignment arm 20 may be constructed to adjust so that the distal end 24 of the alignment arm 20 may be positioned such that the device indicates the proper native version alignment position for the prosthesis.

The base plate 10 has an outer surface 14 and an underside surface 12, wherein the underside surface 12 attaches to the bone 76 to which the prosthesis is to be attached. The outer surface 14 faces away from the bone 76. The base plate 10 may be constructed of any substantially rigid material, which may include but is not limited to metals, metal alloys, plastics, glass, or equivalent materials. The top view shape of the base plate 10 may be of a shape such as a rectangle, square, trapezoid, oval, circle, or equivalent shape. The thickness of the base plate 10 may be in the range from about 0.1 cm to about 10 cm in some examples. In some examples, the thickness of the base plate 10 may be in the range of about 1 cm to about 5 cm. In some examples, the underside surface 12 of the base plate 10 may be flat or concave to reasonably accommodate the curvilinear outer surface of the bone 76 to which the base plate 10 attaches. The outer surface 14 of the base plate 10 may be substantially flat, concave, or convex.

In some examples, as shown in FIGS. 1-5, the outer surface 14 of the base plate 10 may have a groove 16, which may be used to facilitate attachment of the alignment arm 20 to the base plate 10. The groove 16 may be oriented in about the same direction as the bone 76 to which the base plate 10 is attached. The base plate 10 may include fastener(s) 18 to attach the proximal end 22 of the alignment arm 20 to the base plate 10 and/or secure the proximal end 22 of the alignment arm 20 in the groove 16 on the outer surface 14 of the base plate 10. The fastener(s) 18 may be self-contained in the base plate 10. In some examples, the fastener 18 may be self-contained in the central core 30. In some examples, the fastener 18 may be a thumb-tightened screw, set screw, bolt, clip, peg, pin, strap, clamp, and/or a similar fastener. In some examples, a thumb-tightened screw may be used to secure the proximal end 22 of the alignment arm 20 to the base plate 10. The outer surface 14 of the base plate 10 may have graduations along the groove 16 that may be used to determine the desired position of the proximal end 22 of the alignment arm 20, and the graduations may be of any convenient and/or useful unit of measurement.

The underside surface 12 of the base plate 10 may attach to the bone 76 to which the prosthesis is being implanted by using one or more fasteners 70. In some examples, the fastener 70 may be one or more screws with a length in the range of about 0.5 cm to about 5 cm. The screws may also be self-tapping. In some examples, two or more self-tapping screws may be used, where the two screws each may have a length of about 1.25 cm, and the self-tapping screws may be self-contained within the base plate 10, which may prevent the screws from being lost during the surgical procedure. Some examples may include one or more wires to secure the base plate 10 to the bone 76, wherein the wire(s) may attach to the base plate 10 through small holes in the base plate 10. The wires may also extend around the outer surface 14 of the base plate 10. In some examples, the wires may be Kirschner wires. Some examples may employ clamp(s) to attach the base plate 10 to the bone 76. The clamp(s) may be coupled to the base plate 10 and positioned such that tightening the clamps allow the clamps to hold the base plate 10 in position. Some examples may include a bracket with a fastener and/or a strap to attach the base plate 10 to the bone 76.

In some examples, the alignment arm 20 may include interconnected and adjustable pieces having distinct movement point(s) that may be tightened by fasteners into a desired secured position. The alignment arm 20 may be constructed of any suitable materials for performing as described herein, including at least metal, metal alloy, plastic, glass, wood, equivalent materials, or mixtures thereof. In some examples, the alignment arm 20 may include five interconnected parts, which may include a central core 30 coupled to the base plate 10, a horizontal rotation arm 40 coupled to the central core 30 (horizontal with respect to the length of the bone), a vertical swivel arm 50 coupled to and extending perpendicular to the horizontal rotation arm 40 (vertical with respect to the length of the bone), a sliding plate 60 that slides along the vertical swivel arm 50, and a version arm 64 coupled to the sliding plate 60. In these examples, the alignment arm 20 may have four distinct movement points that may allow adjustment in one or more dimensions and may be tightened into a desired position. The horizontal rotation arm 40 is configured to be adjustable horizontally with respect to the base plate 10 and is configured to be rotatably adjustable about the horizontal axis (coaxial with the central core); the vertical swivel arm 50 is configured to be rotatably adjustable about the vertical axis (perpendicular to the central core); and the sliding plate 60 and version arm 64 are configured to be slidably adjustable along the vertical axis. The horizontal adjustability of the horizontal rotation arm 40 may be provided by adjusting the horizontal position of the rotation arm 40 with respect to the central core 30 and/or by adjusting the horizontal position of the central core 30 with respect to the base plate 10.

In some examples, the central core 30 may have an inferior part 32 and a superior part 34, wherein the inferior part 32 may be coupled to the base plate 10 and may be identified as the proximal end 22 of the alignment arm 20. In examples employing a groove 16 in the base plate 10 and a fastener 18 to attach the proximal end 22 of the alignment arm 20 to the base plate 10, the inferior part 32 of the central core 30 may be shaped to fit into the groove 16 and may have a slot 33 to accommodate a fastener 18 while allowing for movement of the central core 30 along the groove 16. In some examples, the fastener 18 may be self-contained in the central core 30. The superior part 34 of the central core 30 may have a hollow cylindrical core 36 and an outer surface 37, wherein the outer surface 37 cross-section may be of any reasonable or desired shape. In some examples, the total length of the central core 30 may be in the range of about 2 cm to about 10 cm, and the length of the superior part 34 may be in the range of about 0.5 cm to about 5 cm. In some examples, the total length may be in the range of about 3 cm to about 4 cm, and the superior part 34 length may be in the range of about 1 cm to about 1.5 cm. In some examples, the inside diameter of the hollow core 36 of the superior part 34 of the central core 30 may be in the range of about 0.25 cm to about 2 cm.

In some examples, the horizontal rotation arm 40 may include a cylindrical rod with an inferior part 42 and a superior part 44. The inferior part 42 may be dimensioned to fit axially within the cylindrical hollow core 36 of the superior part 34 of the central core 30 with tolerances such that the horizontal rotation arm 40 may rotate within the hollow core 36. In some examples, the length of the horizontal rotation arm 40 may be in the range of about 1.5 cm to about 6 cm. The superior part 34 of the central core 30 may have a fastener 38 to secure the position of the horizontal rotation arm 40 at a desired position and/or orientation. In some examples, the fastener 38 may be self-contained in the horizontal rotation arm 40, and in some examples, the fastener 38 may be self-contained in the superior part 34 of the central core 30. In some examples, the superior part 34 of the central core 30 may include a self-contained thumb-tightened set screw to secure the horizontal rotation arm 40 in a desired position. These examples may enable the horizontal rotation arm 40 to rotate in about 360 degrees of movement. In some examples, a fastener 38 that is a thumb-tightened screw may thread into a fixed location on the horizontal rotation arm 40, and the superior part 34 of the central core 30 may have a slot 39 to enable the horizontal rotation arm 40 and fastener 38 to rotate. In some examples, the slot 39 may be large enough to permit about 120 degrees of rotation.

The superior part 44 of the horizontal rotation arm 40 may include a fastener 46 to attach a vertical swivel arm 50 and securing the vertical rotation position of the vertical swivel arm 50 in a desired position and/or orientation. In some examples, the fastener 46 may be a self-contained thumb-tightened screw that threads through a horizontal hole in the superior part 44 of the horizontal rotation arm 40 and into a threaded hole in the proximal end 52 of the vertical swivel arm 50. In some examples, the vertical swivel arm 50 may rotate to a desired position, and once in position, the fastener 46 may be tightened to secure the position of the vertical swivel arm 50 in the desired position. In some examples, the fastener 46 may be self-contained in the vertical swivel arm 50.

In some examples, the vertical swivel arm 50 may have a proximal end 52 and a distal end 54. The proximal end 52 may attach about perpendicular to the superior end 44 of the horizontal rotation arm 40 by way of a fastener 46. In some examples, the fastener 46 may be a self-contained thumb-tightened screw, set screw, bolt, clamp, pin, strap, and/or other fastener. The fastener 46 may be self-contained in the vertical swivel arm 50 and/or may be self-contained in the horizontal rotation arm 40. The proximal end 52 of the vertical swivel arm 50 may have a cylindrical shape and may have a threaded hole 56 in the proximal end 52 to couple it to the superior end 44 of the horizontal rotation arm 40. The threaded hole 56 in the proximal end 52 of the vertical swivel arm 50 may enable the vertical swivel arm 50 to rotate to a desired position, where the fastener 46 may then be tightened to secure the vertical swivel arm 50 in the desired position. In some examples, the length of the proximal end 52 of the vertical swivel arm 50 may be in the range of about 0.5 cm to about 3 cm, and the diameter of the vertical swivel arm 50 may be in the range of about 0.1 cm to about 3 cm. In some examples, the distal end 54 of the vertical swivel arm 50 may be reduced to a half-cylinder cross-section. The length of the distal end 54 of the vertical swivel arm 50 may be in the range of about 2 cm to about 10 cm. In some examples, the distal end 54 of the vertical swivel arm 50 may have two grooves 58 to allow for the interdigitation of a sliding plate 60. In some examples, the distal end 54 of the vertical swivel arm 50 may have a triangular cross-section. The distal end 54 of the vertical swivel arm 50 may be made to have a shape that is conducive to interdigitation of the sliding plate 60.

The sliding plate 60 may be a plate that slides along the distal end 54 of the vertical swivel arm 50. In some examples, the sliding plate 60 may have two ends 62 that extend downward over the edges of the vertical swivel arm 50 such that the sliding plate 60 may interdigitate with the distal end 54 of the vertical swivel arm 50. In some examples, the sliding plate 60 may include a threaded hole 61 in the center for the purpose of securing the position of the sliding plate 60 using a fastener 63. The fastener 63 may be a thumb-tightened screw, screw, bolt, clip, clamp, pin, strap, and/or other suitable fastener. In some examples, the fastener 63 may be self-contained in the vertical swivel arm 50, and in some examples, the fastener 63 may be self-contained in the sliding plate 60. In some examples, the sliding plate 60 may be circular with a radius of about 5% to about 50% of the diameter of the vertical swivel arm 50.

In some examples, the version arm 64 may be a straight arm with a proximal end 66 and a distal end 68. The version arm 64 may be of any reasonable cross-sectional shape and may have a length in the range of about 3 cm to about 10 cm. In some examples, the proximal end 66 of the version arm 64 may include an attachment plate 67, wherein the attachment plate 67 may have a hole in the center. In some examples, the attachment plate 67 with a hole in the center may enable the version arm 64 to couple to the sliding plate 60 with the same fastener 63 that secures the lateral position of the sliding plate 60 on the vertical swivel arm 50. In the aforementioned examples, the positions of the sliding plate 60 and version arm 64 may be secured in desired positions by operation of the single fastener 63.

Figure 11:
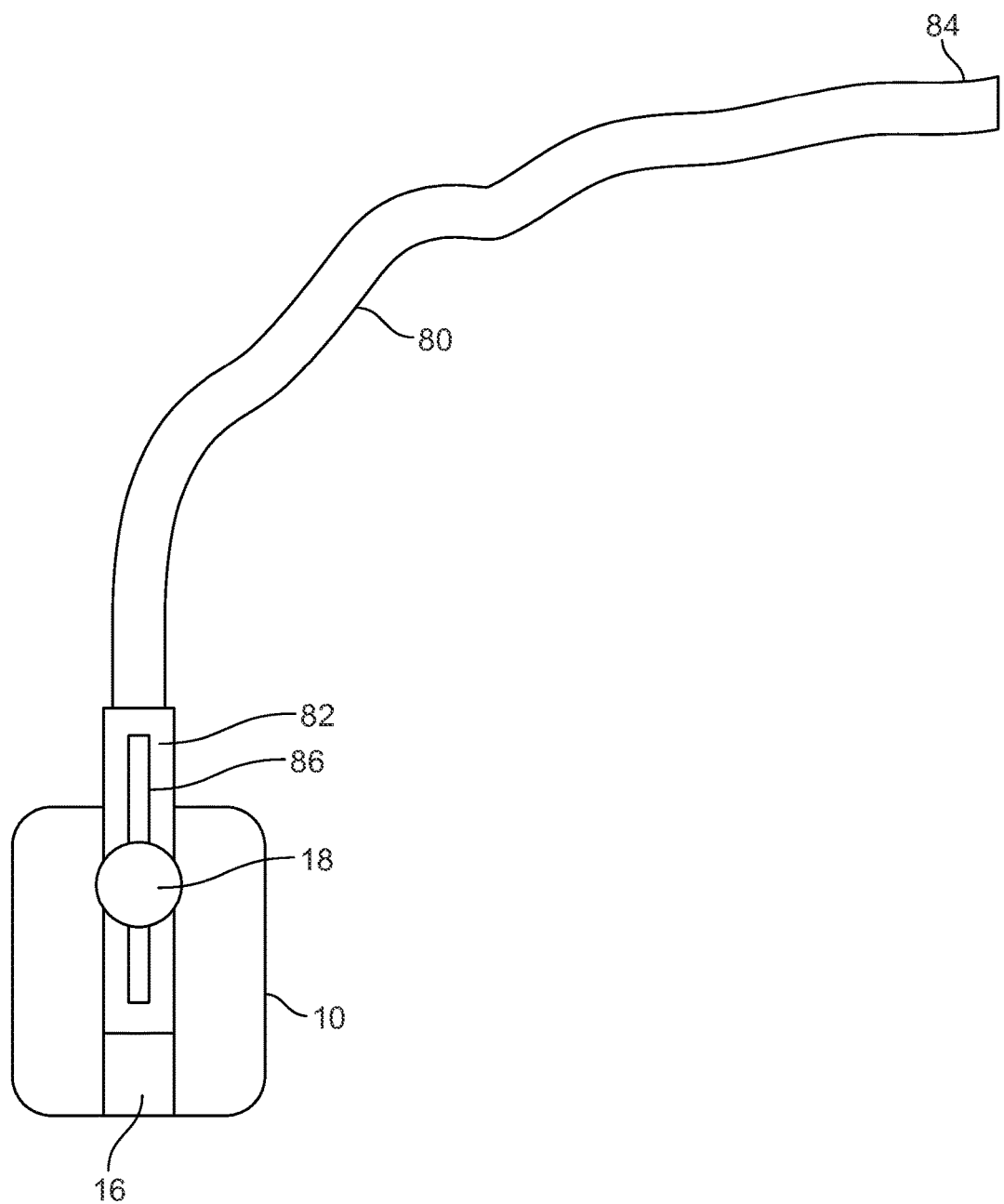
FIG. 11 is a side view of another example alignment device according to the current disclosure, where the alignment arm is a single flexible rod.
Figure 12:
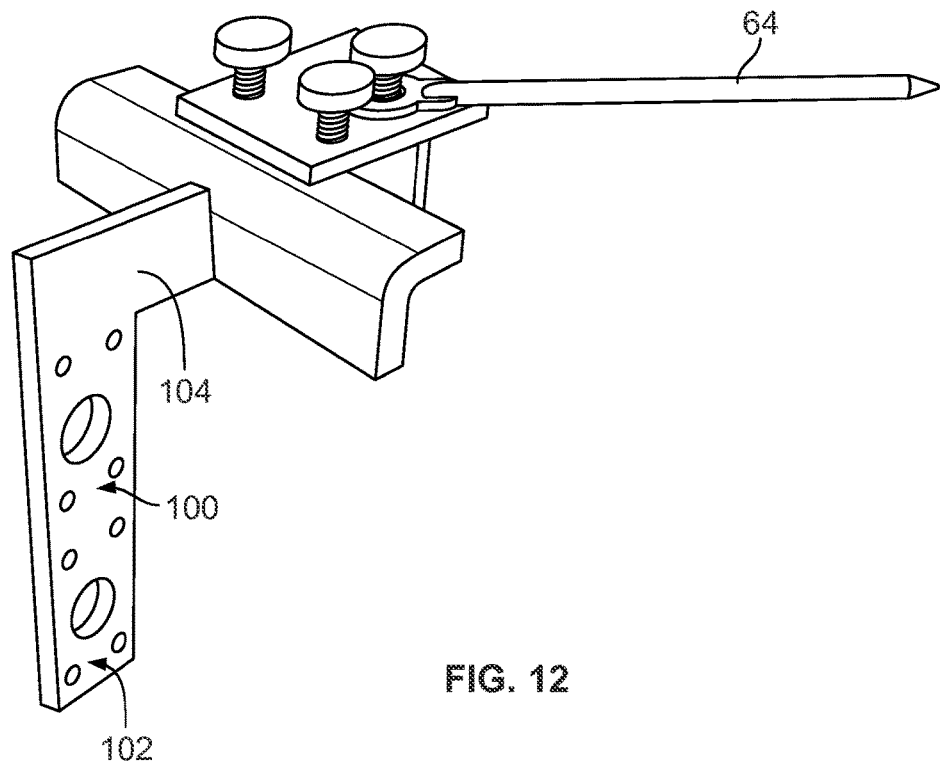
FIG. 12 is a perspective view of another example alignment device according to the current disclosure.
Figure 13:
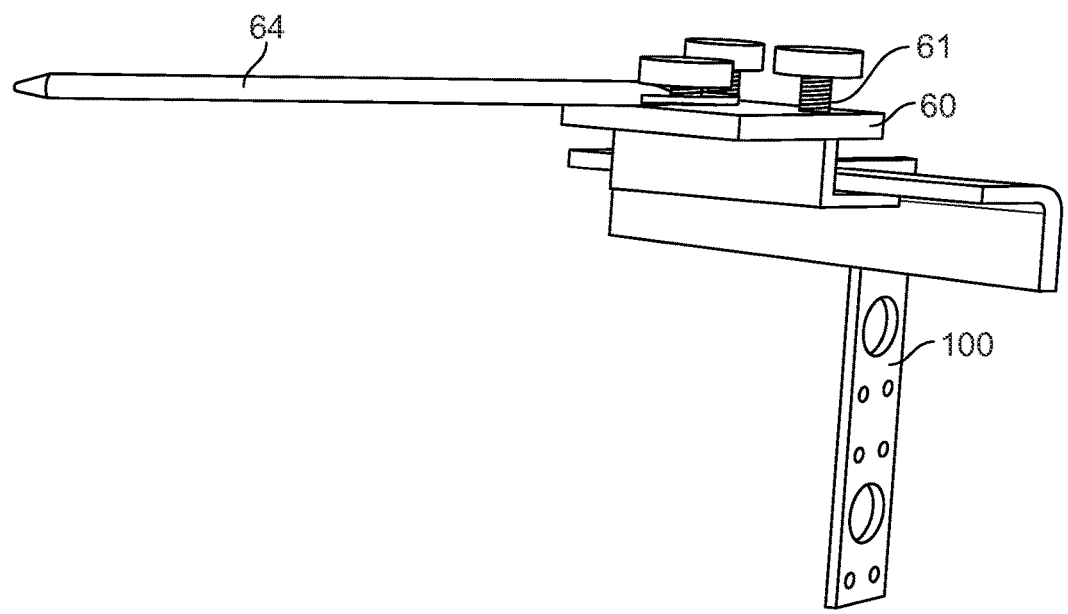
FIG. 13 is another perspective view of the example alignment device of FIG. 12.
Figure 14:
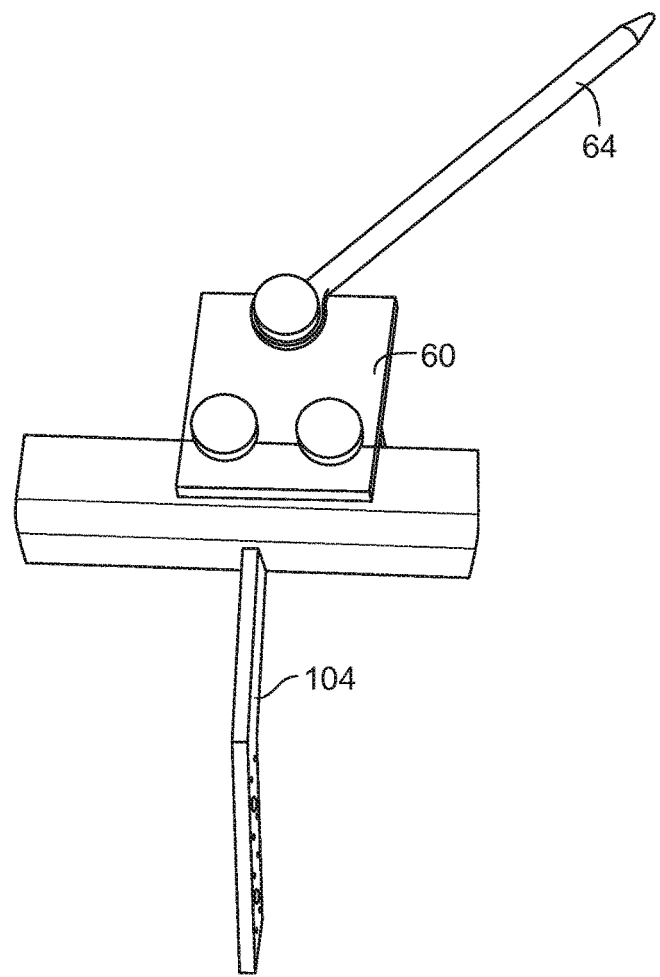
FIG. 14 is a top view of the example alignment device of FIGS. 12 and 13.
Figure 15:
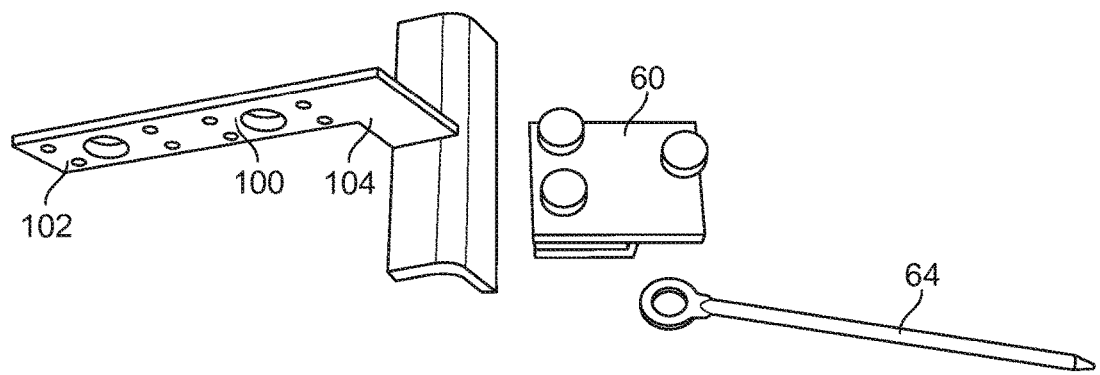
FIG. 15 is a broken-apart view of the example alignment device of FIGS. 12-14.

In some examples, as shown in FIG. 11, the alignment arm 20 may comprise a length of flexible rod 80 having a proximal end 82 and a distal end 84. The flexible rod 80 may be made of metal or plastic. The length of the flexible rod 80 may be in the range of about 6 cm to about 40 cm. The proximal end 82 of the flexible rod may have a rigid attachment part 86 that attaches to the outer surface 14 of the base plate 10 by way of a fastener 18. In some examples where the base plate 10 has a groove 16, the rigid attachment part 86 may be shaped to fit into the groove 16 in the base plate 10. The flexible rod 80 may be manipulated by bending or shaping until the distal end 84 is properly positioned to indicate the desired native version alignment of the bone 76.

Figure 10:
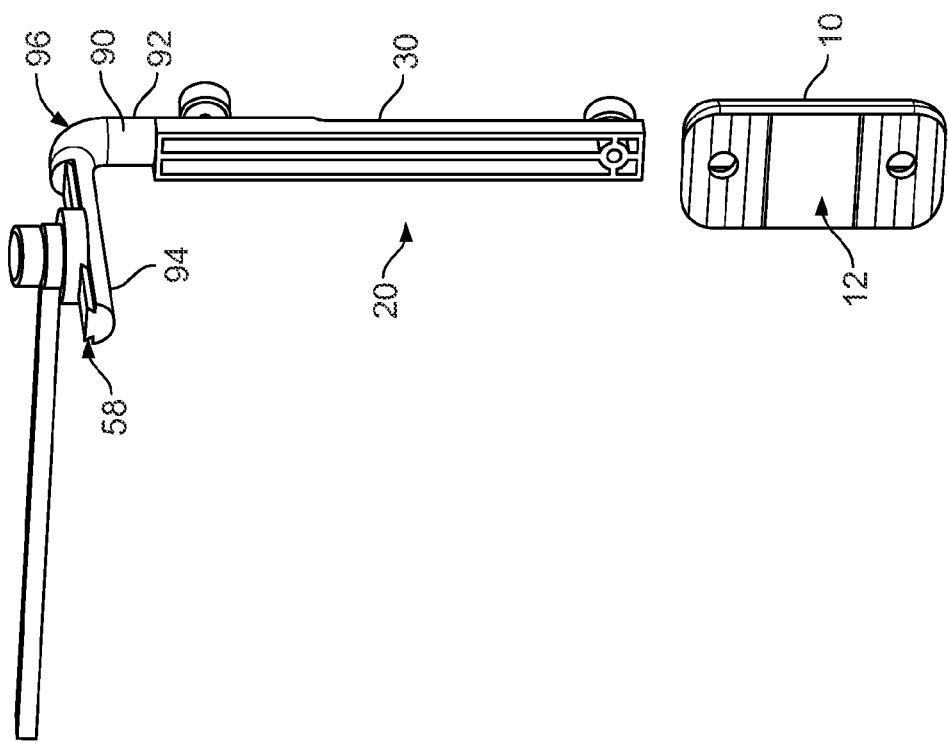
FIG. 10 is another perspective view of the example alignment device of FIG. 9.
Figure 9:
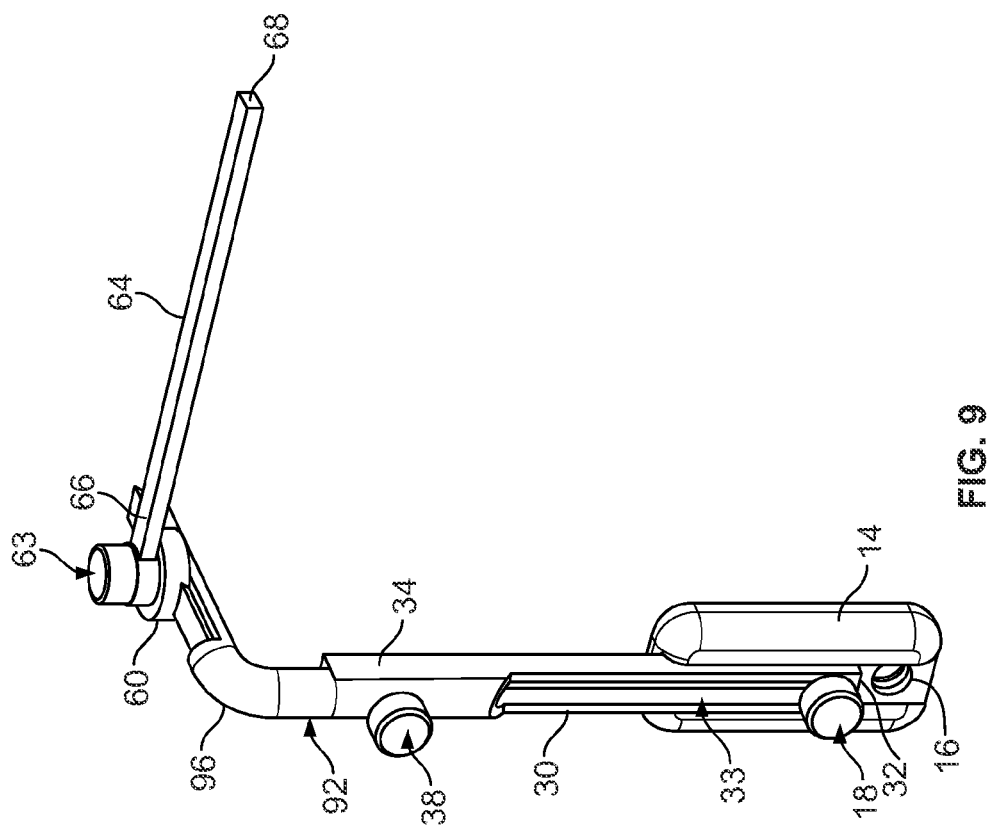
FIG. 9 is a perspective view of another example embodiment of an alignment device according to the current disclosure, where the horizontal rotation arm and vertical swivel arm are combined into a single piece.

In some examples, as shown in FIGS. 9 and 10, the alignment arm 20 may include a central core 30, a horizontal rotation arm 90, a sliding plate 60 and a version arm 64, wherein the horizontal rotation arm 90 may have an inferior, proximal part 92, a superior, distal part 94, and a bend 96 of about 90 degrees. These examples combine the horizontal rotation arm 40 and vertical swivel arm 50 into a single horizontal rotation arm 90 having a bend 96 of about 90 degrees instead of two interconnecting parts. In these examples, the horizontal rotation arm 90 may have an inferior, proximal part 92 and a superior, distal part 94, wherein the inferior, proximal part 92 of the horizontal rotation arm may be cylindrical in shape and dimensioned to fit inside the superior part 34 of the central core 30 with tolerances that allow the horizontal rotation arm 90 to rotate in the superior part 34 of the central core 30. The superior, distal part 94 of the horizontal rotation arm 90 may bend about ninety degrees and extend from about 2 cm to about 10 cm in length. In some examples, the superior, distal part 94 after the bend 96 may be reduced to a half-cylinder cross-section. The sliding plate 60 may interdigitate with the superior, distal part 94 of the horizontal rotation arm 90 having the half-cylindrical cross-section.

In some examples, the alignment arm 20 comprises a central core 30, horizontal rotation arm 40, a vertical swivel arm 50 and a version arm 64, wherein the version arm itself may have an attachment plate 67 that interdigitates directly with the vertical swivel arm 50 rather than incorporating a separate sliding plate 60. These examples combine the sliding plate 60 and version arm 64 assembly of previously described examples into a single piece.

In some examples, as shown in FIGS. 12-15, the central core 30 and base plate 10 may be combined into a single combination base piece 100 having a base part 102 that attaches to the bone 76 and an extension part 104. In these examples, the alignment arm 20 may include a horizontal rotation arm 40, a vertical swivel arm 50, a sliding plate 60, a version arm 64, or combinations thereof. In some examples, the extending part 104 may have a hollow core and vertical adjustment may be accomplished by sliding the horizontal rotation arm 40 up and down inside the hollow core of the extending part 104 of the single combination base piece 100.

In some examples, the base plate 10 may be attached to the bone 76 to which the prosthesis is to be implanted. The position of the central core 30 relative to the base plate 10 may be adjusted to an initial desired position and secured in place using the fastener 18 on the base plate 10. The horizontal rotation arm 40 may be rotated to an approximate desired position and secured in the approximate desired position with another fastener 38. The vertical swivel arm 50 may be rotated into an approximate desired position of the vertical swivel arm 50 and secured into place with a fastener 46 on the superior end 44 of the horizontal rotation arm 40. The sliding plate 60 and version arm 64 may be adjusted to an approximate position such that the distal end 68 of the version arm 64 approximately indicates the native version alignment position of the bone 76. The alignment arm 20 may be adjusted to refine the native version alignment by making small adjustments to the position of the central core 30, horizontal rotation arm 40, vertical swivel arm 50, sliding plate 60, and/or version arm 64 and repeating adjustments, if appropriate, until the alignment arm is in the desired position.

Some examples may be used for a hip arthroplasty surgical procedure. For example, the following operations may be performed after a surgeon has made an incision for a posterior, posterior lateral, or lateral approach to the hip for a hip arthroplasty procedure and dissected off the soft tissue to expose the proximal femur and femoral neck and head: (1) the surgeon applies an example surgical device to the femur by using a screwdriver to screw the two self-contained fasteners 70 into the posterior aspect of the proximal femur just superior-lateral to the lesser trochanter, wherein the fasteners 70 allow the base plate 10 to be secured to the bone 76 and do not allow for rotation of the base plate 10; (2) the alignment arm 20 is then placed into the base plate 10 and the height of the femoral head is measured by tightening the arm apparatus 20 central core 30 to the base plate 10 with the alignment arm 20 lying on the superior aspect of the femoral head; (3) the surgeon records the height of the central core 30 on the base plate 10 using the marked base plate 30 measurements; (4) the horizontal rotation arm 40, vertical swivel arm 50, sliding plate 60, and version arm 64 are all adjusted so that the version arm 70 is centered down the center of the femoral neck and head; (5) the parts are tightened in place once the version arm 64 is centered in correct position with fasteners 38, 46 and 63 that are present at each part junction; (6) once the alignment arm 20 is correctly positioned down the center of the femoral neck and head and tightened in place to secure its position, the surgeon uses an electrocautery device to mark his femoral neck cut by marking a line exactly perpendicular to the alignment arm 20 on the femoral neck; (7) the surgeon then loosens only the central core 30 fastener 18 so that the alignment arm 20 is removed with all of the parts secured in place but leaving the base plate 10 secured to the femur, wherein the surgeon makes sure not to disrupt the alignment of the alignment arm 20 as this is adjusted to the pre-neck cut version; (8) the alignment arm 20 may be placed in a secured place so as not to be disturbed; (9) the surgeon may then make the neck cut according to the marked line; (10) the head may be removed; (11) the alignment arm 20 that is still in its tightened correct position may then be reinserted into the base plate 10; (12) the surgeon then uses electrocautery to mark another line on the cut surface of the femoral neck that is in the exact version alignment as the alignment arm 20; (13) the alignment arm 20 is removed; (14) the surgeon prepares the canal and broaches the canal as usual but using the marked surface as his guide for alignment, but if the surgeon cannot determine the correct version or the cut surface is distorted, the surgeon can always reapply the alignment arm 20 to the base plate 10 to allow for correct version determination; (15) before the final broaches are used in the broaching process, it is recommended that the alignment arm 20 be reapplied to the base plate 10 to make sure the broaches are correctly positioned; (16) the surgeon performs the broaching process; (17) after the broaching process is complete, the alignment arm 20 can be reapplied just before the prosthesis is implanted to guarantee correct version alignment; (18) the central core 30 can be tightened at the pre-recorded height on the base plate 10 and this can help guide how the surgeon makes adjustments for the height of the prosthesis to maintain the native leg length of the patient; and (19) the base plate 10 is then detached from the bone 76.

Some examples may be used during shoulder arthroplasty. An example shoulder arthroplasty technique is similar except the surgical approach and the location of base plate 10 attachment being on the anterior aspect of the proximal humerus. Some examples may be used for other prosthetic implant procedures.

As an example, an example is used on humeri obtained from cadavers. The humeri may be dissected and removed from the cadaver, and the soft tissue may be removed from the bones, especially at the proximal aspect. Both humeri may be inspected for any significant deformities, evidence of previous trauma or fracture, or lesions of any type. Both humeri may be imaged with a CT scanner, and the images may be downloaded to a storage device or storage medium installed with a program that allows for making measurements and angles.

In a biomechanics laboratory the humeri may be secured in place with a vice clamp. The base plate 10 of an example of the disclosure may be secured to the proximal humeral shaft just lateral to the lesser tuberosity. The example's alignment arm 20 may then be positioned down the center of the neck and head with the arm lying on top of the head. The alignment arm 20 may then be securely tightened to maintain position, and a pen may be used to make a mark perpendicular to the alignment arm for the neck cut. The height of the alignment arm 20 on the base plate 10 may be recorded and the alignment arm 20 may be removed from the base plate 10.

Using a total shoulder system surgical set and an oscillating saw, the neck cut may be made perpendicular to the axis of the head and neck using the previously made mark. The head may be removed, and the cut surface may be inspected for any remaining bone or soft tissue needing removal. The alignment arm 20 may then be reattached to the base plate 10. Using a pen, a mark may be made on the cut surface down the center of the cut bone matching the angle of the alignment arm 20. The alignment arm 20 may then be removed, and using the mark on the cut surface, the humeral shaft may be sequentially broached. After the appropriate broach is implanted, the alignment arm 20 may be reattached to the base plate 10, and the broach version may be assessed. The implant may be re-oriented until the version of the implant matches the version of the alignment arm exactly. The same sequence may be undertaken with the other humerus. The broached humeri may then be CT scanned again and the results may be saved to a storage device or storage medium.

Some example may measure the version and use the axis of the humeral head and neck and the bicipital groove. The version may be calculated by first creating a triangular grid based upon three points: (1) the center of the bicipital groove, (2) the lateral aspect of the sclerotic margin of the anterior depression capsule insertion site, and (3) the lateral aspect of the sclerotic margin of the posterior depression capsule insertion site. These three landmarks are found on every pertinent CT slice and are easily identifiable both pre-procedure and post-procedure.

After the triangular grid is made, the pre-procedural head and neck dimensions may be calculated by (1) marking select points on the anterior and posterior aspects of the humeral head that are equal distance to each other and (2) measuring the distance between them. An angle is then created where the first ray starts at the center of the humeral head and evenly transects the marked lines. The angles vertex is the line between the anterior and posterior sclerotic margins of the capsular insertion sites. The second ray then goes to the center of the bicipital groove.

The post-procedural version angle may be made using the same triangular grid, but the first ray may be centered along the central axis of the prosthesis's neck. Making equally distant marks on the neck and coupling them in a manner similar to the head measurements makes the first ray. The first ray may then split these marks at equal distances and run to the vertex from the previously mentioned triangular grid axis. The second ray then may be similar, extending to the center of the bicipital groove.

For accuracy, the version angles may be made on three consecutive CT slices of both the pre-procedural and post-procedural humeri. The CT slices may be matched so that each slice is at the same level to the other using the lesser tuberosity as a landmark. The three pre-procedural version angles may be averaged together and are compared to the results of the post-procedural angles.

In some examples, the base plate 10 may be secured to the proximal humerus with ease, and may be found to be secure to the bone with applied force. After securing the base plate 10, the alignment arm 20 may be attached and adjusted to align down the center of the head and neck and may be tightened in place to maintain alignment. The process of device application and utility in making the neck cut and prosthesis alignment may be quick and may not inhibit the flow of the procedure.

In some examples, the devised measurement system differs from conventional systems in many ways, including that it may use a grid based upon the bicipital groove to find the version angle while conventional systems use the measurement of 9 mm posterior to the posterior aspect of the bicipital groove to signify the central axis of the humeral head. This measurement system may allow for humeral anatomic variations in bicipital groove morphology and neck and head version, and may be found to have reproducible results that allow for measuring humeral alignment on significantly distorted anatomy after the neck cut had been made. The anatomical markers that are used to guide some example grid layouts may be present on all of the CT slices. The CT grid layout may be reproducible for measurement of the implant and humeral head and neck version. Some example pre-implant and post-implant measurements are as follows: the left humerus pre-procedural version angle measures 125.7±2.2 degrees and the left humerus post-procedural version angle measures 124.7±1.9 degrees. The right humerus pre-procedural version angle measures 126.6±2.4 degrees, and the right humerus post-procedural version angle measures 127.5±1.1 degrees. These examples may be effective in aligning a humeral prosthesis in anatomic version. Post-procedure version measurements may be within 2.5 degrees of pre-procedural version measurements. These examples may be easily secured to the humerus and may not increase the procedural time.

In some examples, a surgical device may allow a surgeon to align the femoral and/or humeral prosthesis in the native version of the individual with the use of a version arm that is centered down the center of the head and neck and tightened in position. The version arm may be centered down the head of the bone at the heads center of rotation.

In some examples, the surgical device may allow a surgeon to adjust the prosthesis to match the height of the native humeral and/or femoral head. When the version arm is applied, it may be aligned down the center of the head and neck and may be positioned so that the version arm touches the superior aspect of the head of the bone. After the alignment arm is removed, the neck may be cut, the head and neck may be removed, and the prosthesis may be implanted. The alignment arm may be reapplied and the prosthesis height may be adjusted to match the height of the version arm. This may be accomplished by applying the prosthesis head to the implant, then taking a trial acetabular liner that is the same thickness as the liner that was implanted into the acetabular shell. This may be put on the prosthesis head. The version arm may be at the height of the native head, allowing for the prosthesis to be adjusted to match the native head height. The extremity may then be at the exact length as it was before the surgery.

In some examples, a surgical device may also allow for a surgeon to set the prosthesis in the exact offset as the native joint. The version arm may be marked with 1 millimeter marks, for example, that allow for measurement of the distance from the surgical device's base plate to the very distal end of the head of the bone. When the prosthesis and head are implanted, a trial liner may be applied to allow the surgeon to adjust the prosthesis' offset to match the premeasured offset of the native bone.

In some examples, the base plate and the version arm may both have 1 millimeter marks on them for making measurements. The base plate measurements may measure the height of the alignment arm in the base plate. This may allow for the alignment arm to be reapplied in the exact same height position as it was when the alignment arm was initially applied and tightened in position to measure the height of the native head.

In some examples, the version arm measurements may measure the distance from the base plate to the very distal end of the head of the bone.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. An apparatus for aligning a prosthesis to a native version alignment of a bone, the apparatus comprising:
    a base plate having an outer surface and an underside surface;
    a first fastener configured to couple the underside surface of the base plate to the bone;
    an alignment arm having a proximal end and a distal end and having an ability to adjust in at least three dimensions with respect to the base plate; and
    a second fastener configured to couple the proximal end of the alignment arm to the base plate;
    the alignment arm having a version arm extending from the distal end for indicating the native version alignment of the bone;
    wherein the alignment arm includes:
        a horizontal rotation arm, adjustably mounted horizontally with respect to the base plate, and having an inferior end and a superior end, wherein the horizontal rotation arm is adjustable in a horizontal direction and rotatable along a horizontal axis;
        a vertical swivel arm adjustably coupled to the horizontal rotation arm and configured to be rotatable about a vertical axis perpendicular to the horizontal axis;
        the version arm extending from the vertical swivel arm and mounted so as to be slidable along the vertical swivel arm.

2. The apparatus of claim 1, wherein the alignment arm further includes:
    a first retainer adapted to secure a rotational position of the horizontal rotation arm;
    a second retainer adapted to couple the vertical swivel arm to the horizontal rotation arm; and
    a third retainer adapted to secure a position of the version arm along the vertical swivel arm.

3. The apparatus of claim 1, wherein the alignment arm further includes:
    a sliding plate slidably attached to the vertical swivel arm;
    wherein the third retainer secures a position of the sliding plate along the vertical swivel arm; and
    wherein the version arm is coupled to the sliding plate.

4. A method of determining a native version alignment of a bone, the method comprising:
    providing an alignment device, the device including a base configured to be coupled to the bone, and an alignment arm coupled to the base;
    coupling the base of the alignment device to the bone;
    adjusting the alignment arm such that the alignment device reflects a native version alignment of the bone; and
    aligning a prosthesis in the native version alignment indicated by the alignment device; wherein the alignment arm includes:
    (a) a horizontal rotation arm, adjustably mounted horizontally with respect to the base, the horizontal rotation arm being adjustable in a horizontal direction and rotatable along a horizontal axis,
    (b) a vertical swivel arm adjustably coupled to the horizontal rotation arm and configured to be rotatable about a vertical axis perpendicular to the horizontal axis, and
    (c) a version arm extending from the vertical swivel arm and mounted so as to be slidable along the vertical swivel arm; and
    wherein the method further comprises:
        longitudinally adjusting a position of the horizontal rotation arm relative to the base to an initial horizontal position;
        rotating the horizontal rotation arm with respect to the base from along an axis parallel to the base to an initial horizontal rotation position;
        securing the horizontal rotation arm to the base in the initial horizontal position;
        rotating the vertical swivel arm with respect to the horizontal rotation arm along an axis perpendicular to the horizontal rotation arm to a vertical rotation position;
        securing the vertical swivel arm in the vertical rotation position; and
        adjusting the version arm along the vertical swivel arm to indicate the native version alignment of the bone.

5. A method of aligning a prosthesis to a native version alignment of a bone during a joint surgery, the method comprising:
    making an incision for a desired approach to a joint and the bone;
    dissecting off soft tissue to expose a proximal bone, a bone neck, and a bone head;
    determining a desired aspect of the proximal bone based on a type of joint being replaced;
    coupling a base of a native version alignment device to the proximal bone, the native version alignment device including,
        (a) a horizontal rotation arm, adjustably mounted horizontally with respect to the base, the horizontal rotation arm being adjustable in a horizontal direction and rotatable along a horizontal axis,
        (b) a vertical swivel arm adjustably coupled to the horizontal rotation arm and configured to be rotatable about a vertical axis perpendicular to the horizontal axis, and
        (c) a version arm extending from the vertical swivel arm and mounted so as to be slidable along the vertical swivel arm; and
    adjusting at least one of the horizontal rotation arm, the vertical swivel arm, and the version arm to a native version alignment position.

* * * * *